US00PP36236P2

(12) United States Plant Patent
van Nijnatten

(10) Patent No.: US PP36,236 P2
(45) Date of Patent: Nov. 5, 2024

(54) ***SYRINGA* PLANT NAMED 'Anny200816'**

(50) Latin Name: *Syringa hybrida*
Varietal Denomination: Anny200816

(71) Applicant: André van Nijnatten, Zundert (NL)

(72) Inventor: André van Nijnatten, Zundert (NL)

( * ) Notice: Subject to any disclaimer, the term of this patent is extended or adjusted under 35 U.S.C. 154(b) by 0 days.

(21) Appl. No.: 18/582,732

(22) Filed: Feb. 21, 2024

(30) Foreign Application Priority Data

Jun. 8, 2023 (QZ) ..... PBR 2023/1240

(51) Int. Cl.
*A01H 5/00* (2018.01)
*A01H 6/00* (2018.01)

(52) U.S. Cl.
USPC ..... Plt./248

(58) Field of Classification Search
USPC ..... Plt./248
See application file for complete search history.

*Primary Examiner* — Susan McCormick Ewoldt
(74) *Attorney, Agent, or Firm* — Penny J. Aguirre

(57) ABSTRACT

A new cultivar of *Syringa* plant named 'Anny200816' that is characterized by its compact plant habit and dwarf plant size, its flower panicles that are large in size, its sweet flower fragrance, its short peduncles, its free flowering habit, its flowers that are dark pink in color, and its leaves that are dark green in color.

2 Drawing Sheets

Botanical classification: *Syringa hybrida.*
Variety denomination: 'Anny200816'.

CROSS REFERENCE TO A RELATED APPLICATION

This application claims priority to European Community Plant Variety Office (CPVO) Plant Breeder's Rights application Ser. No. 2023/1240, filed Jun. 8, 2023. The Applicant received the information for the Plant breeders' rights application directly from the Inventor.

BACKGROUND OF THE INVENTION

The present invention relates to a new and distinct cultivar of *Syringa* of hybrid origin that is botanically known as *Syringa* ' Anny200816' and will be referred to hereafter by its cultivar name, 'Anny200816'. 'Anny200816' is a new cultivar of lilac grown for use as an ornamental landscape plant.

'Anny200816' originated as a seedling that arose from seed planted from open pollination of *Syringa* 'Pink Perfume' (U.S. Plant Pat. No. 24,252) in Zundert, The Netherlands in August of 2008. The male parent is therefore unknown.

Asexual propagation of the new cultivar was first accomplished by grafting in 2010 under the direction of the Inventor in Zundert, The Netherlands. Asexual propagation by grafting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Anny200816' as a unique cultivar of *Syringa.*

1. 'Anny200816' exhibits a compact plant habit and dwarf plant size.
2. 'Anny200816' exhibits flower panicles that are large in size.
3. 'Anny200816' exhibits a sweet flower fragrance.
4. 'Anny200816' exhibits short peduncles.
5. 'Anny200816' exhibits free flowering habit.
6. 'Anny200816' exhibits flowers that are dark pink in color.
7. 'Anny200816' exhibits leaves that are dark green in color.

The female parent of 'Anny200816' differs from 'Anny200816' in having longer petioles, a less compact plant habit, flowers that are purple-pink in color, and lighter green leaves. The new *Syringa* can also be compared to *Syringa* cultivars 'Anny2013-18' (U.S. Plant Pat. No. 32,908) and *Syringa meyeri* 'Palibin' (not patented). 'Anny2013-18' differs from 'Anny200816' in having lighter green leaves, slightly longer petioles, flowers that are lighter purple-pink in color, and a less compact plant habit. 'Palibin' differs from 'Anny200816' in having flowers that are lighter in color, a less compact plant habit, lighter green leaves, and longer petioles.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include website listings by Matteo Ragni, Sadzonki, Greenleaf Garden Center, Hoogenraad Handelskwekerijen B.V., Mr. Plant Geek, Visions Pictures, and Plantipp (the breeder's representative for licensing propagators).

BRIEF DESCRIPTION OF THE DRAWINGS

The accompanying color photographs illustrate the overall appearance and distinct characteristics of the new *Syringa*. The photographs were taken of a 2-year-old plant as grown outdoors in a 2-liter container in Zundert, The Netherlands.

The photograph in FIG. 1 provides a side view of a plant of 'Anny200816' in bloom.

Figure 1:
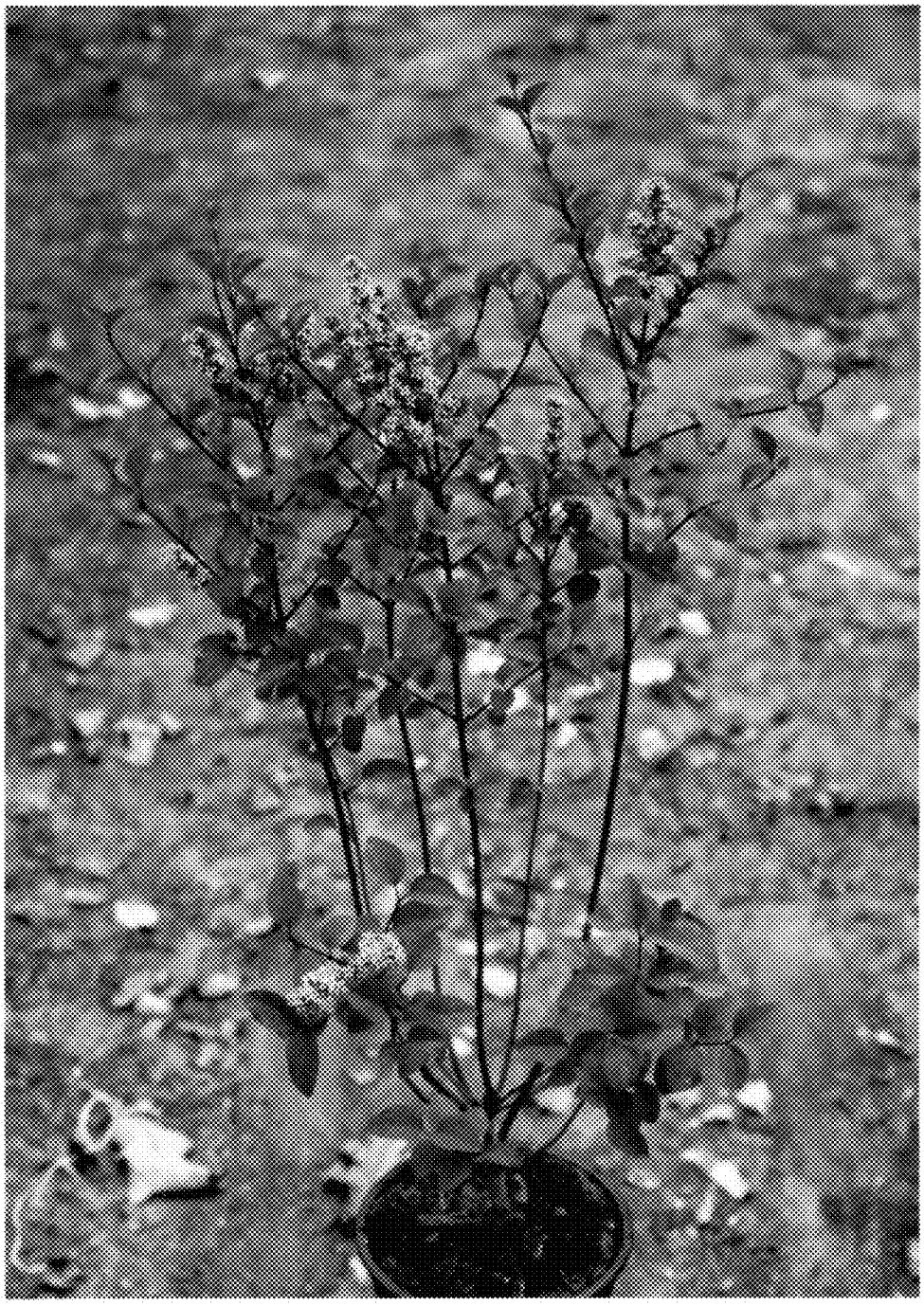
Figure 2:
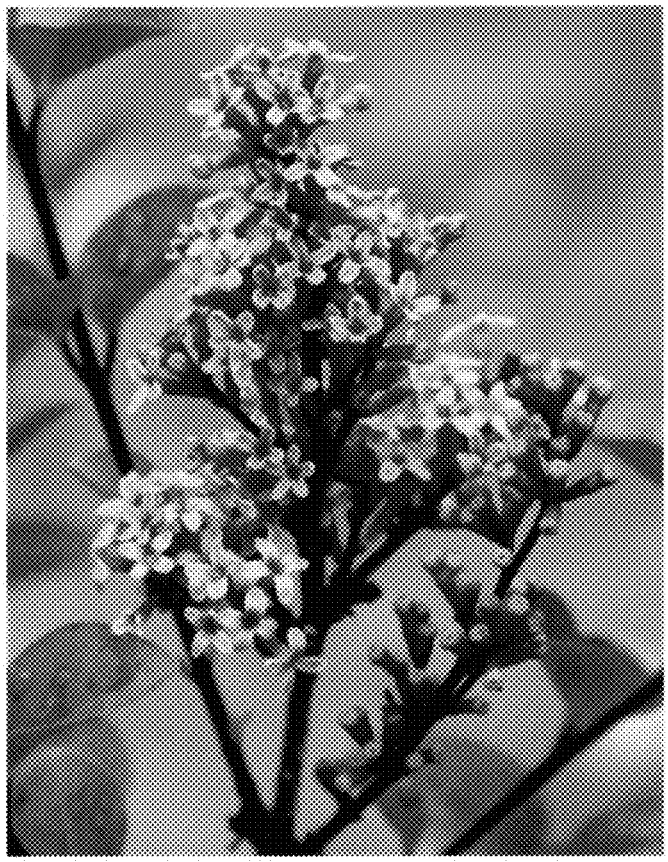

The photograph in FIG. 2 provides a close-up view of an inflorescence of 'Anny200816'.

Figure 3:
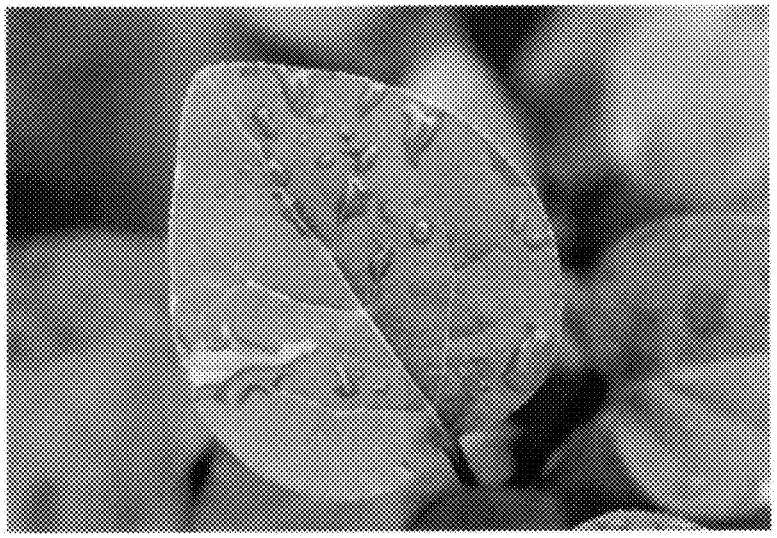

The photograph in FIG. 3 provides a close-up view of a leaf of 'Anny200816'.

The colors in the photographs are as close as possible with the photographic and printing technology utilized and the color values cited in the detailed botanical description accurately describe the colors of the new *Syringa*.

DETAILED BOTANICAL DESCRIPTION

The following is a description of 2-year-old plants as grown outdoors in 2-liter containers in Zundert, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Early summer in The Netherlands.

*Plant type*.—Deciduous shrub.

*Plant habit*.—Compact, dwarf, broadly upright and ovate.

*Height and spread*.—An average of 82.2 cm in height and 27.9 cm-year-old plant in width as a 2-year-old plant grown in a container, reaches as average of 100 cm in height and 80 to 100 cm in spread as a 5-year-old plant in the landscape.

*Hardiness*.—At least in U.S.D.A. Zones 5 to 9.

*Diseases*.—No resistance or susceptibility to diseases has been observed.

*Root description*.—Fibrous and dense, a blend of 165A and 161D in color.

*Propagation*.—Grafting onto rootstock.

*Growth rate*.—Moderate.

*Root development*.—Cuttings from grafting taken in summer root in 4 to 6 weeks, are hardened in winter and plugs are potted into P9 containers in spring.

Branch description:

*Branch shape*.—Rounded.

*Branch color*.—Young and mature; between N186C and 200B, old branches and bark; 148B.

*Branch size*.—Lateral branches; an average of 16.5 cm in length and 3 mm in diameter.

*Branch surface*.—Young and mature; covered with soft pubescent hairs; 0.5 mm in length, NN155C in color, old branches and bark; moderately covered with elliptically shaped lenticels; 1.5 mm in length, 1 mm in width, 199B to 199C.

*Branch strong*.—Strong.

*Branch quantity*.—6 main branches, 7 lateral branches per main branch, an average of 40 lateral branches per plant.

*Internode length*.—Average of 2.9 cm.

*Branching*.—Freely branching, upright.

Foliage description:

*Leaf shape*.—Ovate to cordate.

*Leaf division*.—Simple.

*Leaf base*.—Obtuse to cordate.

*Leaf apex*.—Bluntly acute to retuse.

*Leaf fragrance*.—None.

*Leaf venation*.—Pinnate, upper surface color; 147C, lower surface color; 147D.

*Leaf margins*.—Entire to very finely serrate, slightly undulate.

*Leaf arrangement*.—Opposite.

*Leaf attachment*.—Petiolate.

*Leaf surface*.—Both surfaces are slightly leathery, upper surface is glabrous and lower surface is sparsely pubescent with short hairs; an average of 0.75 mm in length and NN155A in color.

*Leaf size*.—An average of 3 cm in length and 2.6 cm in width.

*Leaf quantity*.—An average of 12 leaves (6 pairs) per lateral branch.

*Leaf color*.—Young upper and lower surface; 146A, mature upper surface; 137B, mature lower surface; 146B to 147B.

*Petioles*.—An average of 9 mm in length and 1.25 mm in width, both surfaces glabrous and slightly glossy, 177A in color.

Inflorescence description:

*Inflorescence type*.—Thyrse compound panicles on terminals and laterals, narrow ovate in overall shape.

*Inflorescence size*.—An average of 8.3 cm (including peduncle) in height and 3.6 cm in width.

*Flower buds*.—Spathulate in shape, an average of 1 cm in length and 2.5 mm diameter, color; 63B, tube 63A to 64B.

*Flower fragrance*.—Strong, pleasant lilac scent.

*Persistence of flowers*.—Self-cleaning.

*Lastingness of flowers*.—Individual panicles last an average of 10 days.

*Flower quantity*.—An average of 75 flowers and buds per lateral stem, average of 1,500 flowers and buds per plant.

*Flower type*.—Salverform, single.

*Flower aspect*.—Upright and slightly outward.

*Flower size*.—An average of 8 mm in diameter and 1 cm in depth.

*Petals*.—4, occasionally 5, salverform, lower part fused into a tube, corolla 4-lobed, an average of 1.1 cm in length and 2 mm in width, narrow oblanceolate in shape, acute apex, margins of free lobes moderately involute, lower 77% fused into tube, both surfaces smooth, upper surface matte, lower surface slightly glossy, color: when opening and fully open upper surface; 67B, margins 67D, tube 63A and 64A, when opening and fully open lower surface; 63B to 64B, tube 63A and 64A.

*Sepals*.—4, rotate, fused into a campanulate shape, entire margins, broad acute apex, 1.5 mm in length, 1 mm in width, color; immature and mature upper and lower surface 183D, lower surface tinged with 153C.

*Calyx*.—Rotate, average of 1.5 mm in length and diameter.

*Peduncles*.—An average of 7.3 cm in length and 1.5 mm in width, held upright, terminal held straight upward, axillary held at an average angle of 25°, moderate strength, 200A in color, surface is matte to slightly glossy, sparsely covered with pubescent hairs; an average of 0.5 mm in length and a color between N155A and surface color.

*Pedicels*.—None, sessile to peduncle.

Reproductive organs:

*Pistils*.—1, average of 2 mm in length, stigma; club shaped, 155A in color, style; average of 1.5 mm in length, 65D in color, ovary; 146A in color.

*Stamens*.—2, anthers; average of 2 mm in length, dorsifixed, sessile (no filament) and implanted into inner side of tube, N77B in color, filaments; none, pollen; moderate in quantity and 4B in color.

*Fruit and seed*.—No seed or fruit produced to date.

It is claimed:

1. A new and distinct cultivar of *Syringa* plant named 'Anny200816' as herein illustrated and described.

* * * * *